United States Patent [19]

Alexander

[11] 3,941,805

[45] Mar. 2, 1976

[54] 3-HALOMETHYLCARBONYL-9-BENZOYL-1,2,3,4-TETRAHYDROCARBAZOLES

[75] Inventor: Ernest John Alexander, East Greenbush, N.Y.

[73] Assignee: Sterling Drug Inc., New York, N.Y.

[22] Filed: Feb. 20, 1974

[21] Appl. No.: 444,165

Related U.S. Application Data

[63] Continuation-in-part of Ser. No. 307,477, Nov. 17, 1972, Pat. No. 3,835,152.

[52] U.S. Cl. ............................... 260/315; 424/274
[51] Int. Cl.$^2$ ....................................... C07D 209/86
[58] Field of Search ..................... 260/315; 307/477

[56] References Cited
UNITED STATES PATENTS

| | | | |
|---|---|---|---|
| 3,655,697 | 4/1972 | Shen et al. | 260/315 |
| 3,687,969 | 8/1972 | Alexander et al. | 260/315 |
| 3,824,314 | 7/1974 | Lacoume | 260/315 |

OTHER PUBLICATIONS

Synthetic Organic Chemistry (1953) Wagner et al. pp. 95, 566, 567.

*Primary Examiner*—Sherman D. Winters
*Attorney, Agent, or Firm*—Frederik W. Stonner; B. Woodrow Wyatt

[57] ABSTRACT

Novel 3-Z-9-benzoyl-1,2,3,4-tetrahydrocarbazoles, wherein Z is $CONR_5R_6$, CONHOH, CN, or $COCH_2X$, where X is chloro or bromo, having antimicrobial and/or anti-inflammatory activity are disclosed. Compounds wherein Z is $CONR_5R_6$ and CONHOH are prepared from the corresponding 3-carboxylic acids by conversion to the corresponding acid chlorides and subsequent reaction with the appropriate amines and hydroxylamine respectively; compounds where Z is CN are prepared by the dehydration of the corresponding compounds where Z is $CONH_2$; and the compounds where Z is $COCH_2X$ are prepared by reacting hydrogen chloride or bromide with the corresponding compounds where Z is $COCHN_2$ which in turn is prepared from the corresponding 3-carboxylic acid chloride by reaction with diazomethane.

5 Claims, No Drawings

3-HALOMETHYLCARBONYL-9-BENZOYL-1,2,3,4-TETRAHYDROCARBAZOLES

This application is a continuation-in-part of prior copending application Ser. No. 307,477, filed November 17, 1972, now U.S. Pat. No. 3,835,152, issued Sept. 10, 1974.

This invention relates to compositions of matter classified in the art of chemistry as 1,2,3,4-tetrahydrocarbazoles.

The compounds of this invention are useful as antimicrobial agents and/or anti-inflammatory agents as more fully described hereinbelow.

In one aspect the invention sought to be patented resides in the novel chemical compounds designated as 3-Z-9-($R_3R_4$-benzoyl)-$R_1$-$R_2$-1,2,3,4-tetrahydrocarbazoles having the formula:

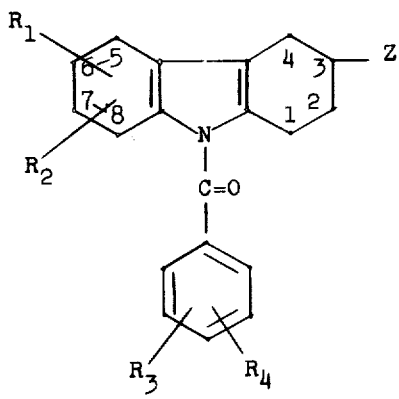

wherein
Z is $CONR_5R_6$, CONHOH, CN, or $COCH_2X$, where $R_1$, $R_2$, $R_3$, $R_4$, $R_5$ and $R_6$ are each hydrogen or lower-alkyl, and X is chloro or bromo.

In a second aspect the invention sought to be patented resides in the novel chemical compounds designated as 3-diazomethylcarbonyl-9-($R'_3$-$R'_4$-benzoyl)-$R'_1$-$R'_2$-1,2,3,4-tetrahydrocarbazoles having the formula:

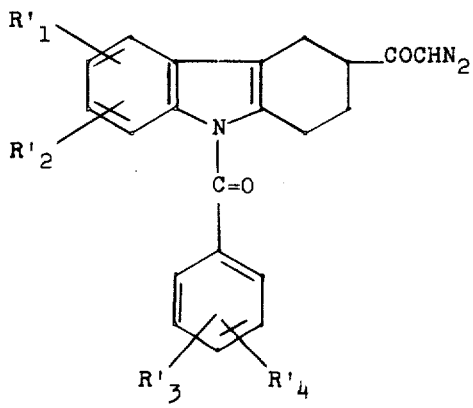

wherein
$R'_1$, $R'_2$, $R'_3$ and $R'_4$ are each hydrogen or loweralkyl.

The compounds having formula II are useful as intermediates in the preparation of the compounds of formula I where Z is $COCH_2X$.

The novel compounds of this invention having formula I wherein Z is $CONR_5R_6$ and CONHOH are prepared from the 9-($R'_3$-$R'_4$-benzoyl)-$R'_1$-$R'_2$-1,2,3,4-tetrahydrocarbazole3-carboxylic acid halide (III), where $R'_1$, $R'_2$, $R'_3$ and $R'_4$ have the meaning defined hereinbefore for formula II and halide is chloride or bromide, by reaction respectively with the amine $NHR_5R_6$ (IV) or hydroxylamine. The reaction can be carried out by treating the acid halide III in a suitable inert solvent, e.g., benzene or pyridine, with at least one equivalent of amine IV or hydroxylamine in the presence of at least one equivalent of a suitable acid-acceptor, e.g., triethylamine, pyridine or potassium bicarbonate. If desired, excess amine IV or hydroxylamine may be used as the acid-acceptor. The reaction can be conveniently carried out be reacting the acid halide III with at least two equivalents of the amine IV or hydroxylamine in a stirred mixture of water and ether for about ten minutes to about one hour.

The novel compounds of formula I where Z is CN are prepared by dehydration of the corresponding 3-carbamyl-9-($R_3$-$R_4$-benzoyl)-$R_1$-$R_2$-1,2,3,4-tetrahydrocarbazole (I,Z = $CONH_2$). The reaction is carried out in a suitable solvent, e.g., benzene or pyridine, in the presence of at least one equivalent of an acid-acceptor, e.g., pyridine or triethylamine, and a suitable dehydrating agent, e.g., phosphorus oxychloride, thionyl chloride or benzenesulphonyl chloride preferably at elevated temperatures. The reaction can be conveniently carried out by treating the 3-carbamyl compund in pyridine with benzenesulphonyl chloride on a steam bath for about one to two hours.

The novel compounds of formula I where Z is $COCH_2X$ are prepared from the corresponding 3-diazomethylcarbonyl-9-($R'_3$-$R'_4$-benzoyl)-$R'_1$-$R'_2$-1,2,3,4-tetrahydrocarbazole (II) by reaction with HX, where X is chloro or bromo, viz., hydrogen chloride or hydrogen bromide. The reaction is carried out with at least one equivalent of hydrogen chloride or hydrogen bromide in a suitable inert solvent, e.g., benzene, ether or toluene, preferably at room temperature. The reaction is conveniently carried out by treating a solution of II in benzene with about one equivalent of either ethereal or gaseous hydrogen chloride or hydrogen bromide at room temperature.

The intermediate 3-diazomethylcarbonyl compound II is prepared from the corresponding acid halide III by reaction in a suitable solvent, e.g., benzene or ether, with at least two equivalents of diazomethane preferably at temperatures ranging from about 0°C. to about room temperature. The reaction is conveniently carried out by reacting the acid halide III with about a three to four mole excess of diazomethane in ehter with ice bath cooling.

The intermediate acid halide III is prepared from the corresponding 9-($R'_3$-$R'_4$-benzoyl)-$R'_1R'_2$-1,2,3,4-tetrahydrocarbazole-3-carboxylic acids using standard procedures, e.g., by reaction in a suitable solvent, e.g., ethylene dichloride or chloroform, with an appropriate halogenating agent such as thionyl chloride or oxalyl chloride.

The 9-($R'_3$-$R'_4$-benzoyl)-$R'_1$-$R'_2$-1,2,3,4-tetrahydrocarbazole-3-carboxylic acids and intermediates therefore belong to classes of compounds which, together with detailed methods for their preparation, are disclosed in U.S. Pat. No. 3,687,969. Thus they are prepared, for example, by condensing the appropriate 1-($R'_3$-$R'_4$-benzoyl)-1-($R'_1$-$R'_2$-phenyl)hydrazine (V), where $R'_1$, $R'_2$, $R'_3$ and $R'_4$ have the meaning defined hereinbefore for compounds of formula II, with cyclohexanone4-carboxylic acid; the intermediate benzoylhydraxine V is prepared by reaction of the $R'_3$-$R'_4$-benzoyl chloride (VI) with an appropriate hydrazone of $R'_1$-$R'_2$-phenylhydrazine (VII) and subsequent alcoholysis; the intermediate benzoyl chlorides VI and phenylhydrazines VII are known compounds or are prepared from corresponding known benzoic acids and anilines respectively.

As used throughout this specification, the term lower-alkyl means such a group containing from one to six carbon atoms which can be arranged as straight or branched chains, and, without limiting the generality of the foregoing, are illustrated by methyl, ethyl, propyl, isopropyl, butyl, sec-butyl, tert-butyl, amyl, hexyl and the like.

It will be understood that in the compounds of formulas I and II the substituents $R_1$ and $R_2$, and $R'_1$ and $R'_2$, respectively, as hereinbefore defined, can each occur at any one of the available carbon atoms at the 6,7,8 and 9 positions, and that the substituents $R_3$ and $R_4$, and $R'_3$ and $R'_4$, respectively, as hereinbefore defined, can each occur at any one of the available carbon atoms of the phenyl ring of the 9-benzoyl group, and in each case when there are two such substituents they can occur in any position combination relative to each other.

The compounds of formula I where Z is $CONR_5R_6$ or $COCH_2X$ possess useful antibacterial activity; and the compounds of formula I where Z is CN possess useful antifungal activity, thus indicating the utility of the former as antibacterial agents and of the latter as antifungal agents.

The antibacterial and antifungal activities were determined using a modification of the Autotiter method described by Goss et al., Applied Microbiology 16 (No. 9), 1414–1416 (1968) in which a 1000 mcg./ml. solution of the test compound is prepared. To the first cup of the Autotray is added 0.1 ml. of the test solution. Activation of the Autotiter initiates a sequence of operations by which 0.05 ml. of the test compound solution is withdrawn from this cup by a Microtiter transfer loop and diluted in 0.05 ml. of sterile semi-synthetic medium (glucose). After this operation, 0.05 ml. of inoculated semi-synthetic medium is added automatically to each cup. The overall operation results in final drug concentrations ranging from 500 to 0.06 mcg./ml. in twofold decrements. The Autotray is incubated for 18–20 hours at 37°C., at which time the trays are examined visually for growth as evidenced by turbidity, and the concentration of the last sample in the series showing no growth (or no turbidity) is recorded as the minimal inhibitory concentration (MIC).

By way of illustration, the compounds of Example 2 (formula I, Z = $CONH_2$, $R_1 = R_2 = R_3 = R_4 = H$) and Example 6 (formula I, Z = $COCH_2X$, X = Cl, $R_1 = R_2 = R_3 = R_4 = H$) were found to be antibacterially effective against Staphlococcus aureus at concentrations of 62.5 mcg./ml. and 0.8 mcg./ml. respectively; and the compound of Example 4 (formula I, Z = CN, $R_1 = R_2 = R_3 = R_4 = H$) was found to be antifungally effective against Aspergillus niger at a concentration of 250 mcg./ml.

The compounds of this invention having formula I where Z is $CONR_5R_6$ or CONHOH exhibit anti-inflammatory activity in one or both of the pharmacological test procedures described hereinbelow, thus indicating their usefulness as anti-inflammatory agents.

The following are brief descriptions of the pharmacological test procedures used to determine anti-inflammatory activity.

INHIBITION OF CARRAGEENIN-INDUCED FOOT EDEMA IN RATS

Young male rats weighting 100–110 g. are used. Food is withdrawn approximately 18 hours prior to medication but the animals are permitted free access to drinking water up to the time of medication. Drugs to be tested are suspended by triturating in 1% gum tragacanth using ground glass homogenizers and administered by gavage in a volume of 1 ml./100 g. body weight. Control animals receive the gum tragacanth only. One hour after medication, 0.05 ml. of 1% suspension of carrageenin in 0.9% saline is injected into the plantar tissue of the left hind paw. Three hours after injection of the carrageenin, edema formation, i.e., increase in foot volume (difference between left hind paw and the uninjected right hind paw) is measured plethysmographically in the unaesthetized rat.

INHIBITION ADJUVANT-INDUCED ARTHRITIS IN RATS

Adult male rats weighing 200–230 g. are used. Adjuvant (M. butyricum), 0.1 ml. of a 0.6% suspension in heavy mineral oil, is injected into the plantar tissue of the left hind paw. A negative control group is injected with mineral oil only. Beginning on the ninth day after adjuvant injection (polyarthritis does not appear until approximately the tenth day after adjuvant administration), the animals receive 12 daily medications of test compound suspended by triturating in 1% gum tragacanth using a ground glass homogenizer and administered by gavage in a volume of 1 ml./100 g. body weight. Both the negative control and adjuvant injected control animals receive the vehicle only. Food and water are permitted ad libitum. Twenty-four hours after the last mediciation, the animals are weighed, the degree of arthritic involvement, i.e., increase in foot volume and plasma inflammation units are determined. Foot volume is measured plethysmographically in the unanesthetized rat.

By way of illustration, the compound of Example 2 (formula I, Z = $CONH_2$, $R_1 = R_2 = R_3 = R_4 = H$) when tested in the Adjuvant-Induced Arthritis test procedure, and the compound of Example 3 (formula I, Z = CONHOH, $R_1 = R_2 = R_3 = R_4 = H$) when tested in the Adjuvant-Induced Arthritis and Carrageenin-Induced Foot Edema test procedures, were found to be effective anti-inflammatory agents when administered in the amount of 103 mg. and 108 mg. per kilogram of body weight per dosage unit respectively.

The actual determination of the numerical biological data definitive for a particular compound is readily determined by standard test procedures by technicians having ordinary skill in pharmacological test procedures, without the need for any extensive experimentation.

The compounds of the invention having antibacterial and antifungal activity can be formulated for use by preparing a dilute solution in an aqueous medium or in a solution containing a surfactant, or alternatively in an organic medium in which the compounds are soluble, the example ethyl alcohol, and are applied to a surface to be disinfected by conventional means such as spraying, swabbing immersion, and the like. Alternatively the compounds can be formulated as ointments or creams by incorporating them in conventional ointment or cream bases, for example alkylpolyether alcohols, cetyl alcohol, stearyl alcohol, and the like, or as jellies by incorporating them in conventional jelly bases as glycerol and tragacanth. They can also be formulated for use as aerosol sprays or foams.

The compounds of this invention having anti-inflammatory activity can be prepared for use by conventional pharmaceutical procedures; that is, they can be incorporated in unit dosage form in tablets or capsules for oral administration either alone or in combination with suitable adjuvants such as calcium carbonate, starch, lactose, talc, magnesium stearate, gum acacia, and the like; or as aqueous or oil suspensions or solutions in a pharmaceutically acceptable vehicle such as aqueous alcohol, glycol, oil solutions or oil-water emulsions for oral or parenteral administration.

The molecular structures of the compounds of this invention were assigned on the basis of the method of their synthesis and study of their infrared spectra, and confirmed by the correspondence between calculated and found values for the elementary analysis for representative examples.

The invention is illustrated by the following examples without, however, being limited thereto.

EXAMPLE 1

A mixture of 32 g. of 9-benzoyl-1,2,3,4-tetrahydrocarbazole-3-carboxylic acid in 100 ml. of dry ethylene dichloride was treated with 17 ml. thionyl chloride containing two drops of dimethylformamide and stirred on a warm water bath for two hours. The clear solution was evaporated under reduced pressure and the resulting residual oil was treated with a small amount of ether. The resulting crystals were collected by filtration, washed with cool ether, diluted with pentane and dried under reduced pressure at 50°C. to yield 31.8 g. of 9-benzoyl-1,2,3,4-tetrahydrocarbazole-3-carboxylic acid chloride, m.p. 109°–110°C.

EXAMPLE 2

To a stirred mixture of 75 ml. concentrated ammonium hydroxide, 100 ml. water, ice and 100 ml. ether was added 10.2 g. of solid 9-benzoyl-1,2,3,4-tetrahydrocarbazole-3-carboxylic acid chloride, and the mixture was stirred vigorously for ten minutes. The ether was evaporated by passing air through the mixture and the resulting solid was collected by filtration, washed with water ans suspended in hot acetone. The acetone suspension was diluted with water, cooled, and the solid was collected by filtration and was recrystallized from dimethylformamide in water to give 8.8 g. of 3-carbamyl-9-benzoyl-1,2,3,4-tetrahydrocarbazole, m.p. 228°–230°C.

EXAMPLE 3

A suspension of hydroxylamine, prepared by treating 15 g. of hydroxylamine hydrochloride in 100 ml. of water and 100 ml. of ether with 100 ml. of 10% potassium bicarbonate solution, was treated with 3.4 g. of solid 9-benzoyl-1,2,3,4-tetrahydrocarbazole-3-carboxylic acid chloride with stirring. The either was evaporated by passing air through the mixture and the resulting solid was collected by filtration and washed with water. The solution of this solid in acetate was washed with water, dried over magnesium sulfate and evaporated to dryness under reduced pressure. The residual oil was dissolved in acetone, concentrated, diluted with benzene and further concentrated to evaporate the acetone. The resulting solid (2.9 g.) was collected by filtration and recrystallized from ethyl acetate-heptane to give 2.61 g. of 3-hydroxyaminocarbonyl9-benzoyl-1,2,3,4-tetrahydrocarbazole, m.p. 182°–184°C.

EXAMPLE 4

3-Carbamyl-9-benzoyl-1,2,3,4-tetrahydrocarbazole (6.4 g.) in 40 ml. dry pyrindine was treated with 3.5 ml. benzenesulphonyl chloride and the solution was warmed on a steam bath for one hour, cooled and diluted with water. The resulting solid was collected by filtration, washed with water and recrystallized from acetone-water to give 4.8 g. of 3-cyano-9-benzoyl-1,2,3,4-tetrahydrocarbazole, m.p. 145°–147°C.

EXAMPLE 5

To a stirred, dry, cold solution of 6 g. of diazomethane in 200 ml. of ether was added 10 g. of solid 9-benzoyl-1,2,3,4-tetrahydrocarbazole-3-carboxylic acid chloride which slowly dissolved. Stirring was continued for about 30 minutes and the resulting mixture was diluted with pentane and the solids were collected by filtration and recrystallized from benzenepentane to yield 7.8 g. of 3-diazomethylcarbonyl-9-benzoyl-1,2,3,4-tetrahydrocarbazole, m.p. 134°–136°C.

EXAMPLE 6

To a solution of 10 g. of 3-diazomethylcarbonyl-9-benzoyl-1,2,3,4-tetrahydrocarbazole in 15 ml. benzene was added in small portions a slight excess of ethereal hydrogen chloride. The resulting mixture was diluted with hexane. The solids were collected by filtration and recrystallized from benzenehexane to give 8.7 g. of 3-chloromethylcarbonyl-9-benzoyl-1,2,3,4-tetrahydrocarbazole, m.p. 140°–142°C.

Following the procedure described in Example 1 but substituting for 9-benzoyl-1,2,3,4-tetrahydrocarbazole-3-carboxylic acid an equivalent amount of the 9-(R'$_3$-R'$_4$-benzoyl)- R'$_1$-R'$_2$-1,2,3,4-tetrahydrocarbazole-3-carboxylic acids listed in Table I below, there are obtained respectively the corresponding 9-(R'$_3$-R'$_4$-benzoyl)-R'$_1$-R'$_2$-1,2,3,4-tetrahydrocarbazole-3-carboxylic acid chlorides:

TABLE I 9-(R′₃-R′₄-benzoyl)-R′₁-R′₂-1,2,3,4-tetrahydrocarbazole-3-carboxylic acid

| | R′₁-R′₂ | R′₃-R′₄ |
|---|---|---|
| 7. | 6-methyl | H |
| 8. | 6-tert-butyl | 4-methyl |
| 9. | 5,8-dimethyl | 3,4-dimethyl |
| 10. | 6-hexyl | 4-tert-butyl |
| 11. | H | 4-hexyl |
| 12. | 8-ethyl | H |

The tetrahydrocarbazole-3-carboxylic acids listed in Table I above are prepared by condensation of cyclohexanone-4-carboxylic acid with the corresponding 1-(R′₃-R′₄-benzoyl)-1-(R′₁-R′₂-phenyl)hydrazines listed in Table II.

TABLE II 1-(R′₃-R′₄-benzoyl)-1-(R′₁-R′₂-phenyl)hydrazine

| R′₁-R′₂ | R′₃-R′₄ |
|---|---|
| 4-methyl | H |
| 4-tert-butyl | 4-methyl |
| 2,5-dimethyl | 3,4-dimethyl |
| 4-hexyl | 4-tert-butyl |
| H | 4-hexyl |
| 2-ethyl | H |

The benzoylhydrazines listed in Table II are prepared by reaction of the appropriate hydrazones, e.g., acetaldehyde hydrazones, of the corresponding R′₁-R′₂-phenylhydrazines, wherein R′₁ and R′₂ are the same as indicated for R′₁-R′₂ in Table II, with the corresponding R′₃-R′₄-benzoyl chlorides, wherein R′₃ and R′₄ are the same as indicated for R′₃-R′₄ in Table II and subsequent alcoholysis. The methods of preparation of 9-(R′₃-R′₄-benzoyl)-R′₁-R′₂-1,2,3,4-tetrahydrocarbazole-3-carboxylic acid; 1-(R′₃-R′₄-benzoyl)-1-(R′₁-R′₂-phenyl)hydrazine; R′₁-R′₂-phenylhydrazine; and R′₃-R′₄-benzoyl chloride have been described in U.S. Pat. No. 3,687,969.

Following the procedure described in Example 2 but substituting for 9-benzoyl-1,2,3,4-tetrahydrocarbazole-3-carboxylic acid chloride an equivalent amount of the acid chlorides of the 3-carboxylic acids 7–12 listed in Table I there are obtained respectively: 13. 3-carbamyl-9-benzoyl-6-methyl-1,2,3,4-tetrahydrocarbazole;

14. 3-carbamyl-9-(4-toluoyl)-6-tert-butyl-1,2,3,4-tetrahydrocarbazole;

15. 3-carbamyl-9-(3,4-dimethylbenzoyl)-5,8-dimethyl-1,2,3,4-tetrahydrocarbazole;

16. 3-carbamyl-9-(4-tert-butylbenzoyl)-6-hexyl-1,2,3,4-tetrahydrocarbazole;

17. 3-carbamyl-9-(4-hexylbenzoyl)-1,2,3,4-tetrahydrocarbazole; and 18. 3-carbamyl-9-(benzoyl)-8-ethyl-1,2,3,4-tetrahydrocarbazole.

Following the procedure described in Example 3 but substituting for 9-benzoyl-1,2,3,4-tetrahydrocarbazole-3-carboxylic acid chloride an equivalent amount of the acid chlorides of the carboxylic acids 7–12 listed in Table I above there are obtained respectively:

19. 3-hydroxyaminocarbonyl-9-benzoyl-6-methyl-1,2,3,4-tetrahydrocarbazole;

20. 3-hydroxyaminocarbonyl-9-(4-toluoyl)-6-tert-butyl-1,2,3,4-tetrahydrocarbazole;

21. 3-hydroxyaminocarbonyl-9-(3,4-dimethylbenzoyl)-5,8-dimethyl-1,2,3,4-tetrahydrocarbazole;

22. 3-hydroxyaminocarbonyl-9-(4-tert-butylbenzoyl)-6-hexyl-1,2,3,4-tetrahydrocarbazole;

23. 3-hydroxyaminocarbonyl-9-(4-hexylbenzoyl)-1,2,3,4-tetrahydrocarbazole; and 24. 3-hydroxyaminocarbonyl-9-(benzoyl)-8-ethyl-1,2,3,4-tetrahydrocarbazole.

Following the procedure described in Example 5 but substituting for 9-benzoyl-1,2,3,4-tetrahydrocarbazole-3-carboxylic acid chloride the acid chlorides of the carboxylic acids 7–12 listed in Table I above there are obtained respectively:

25. 3-diazomethylcarbonyl-9-benzoyl-6-methyl-1,2,3,4-tetrahydrocarbazole;

26. 3-diazomethylcarbonyl-9-(4-toluoyl)-6-tert-butyl-1,2,3,4-tetrahydrocarbazole;

27. 3-diazomethylcarbonyl-9-(3,4-dimethylbenzoyl)-5,8-dimethyl-1,2,3,4-tetrahydrocarbazole;

28. 3-diazomethylcarbonyl-9-(4-tert-butylbenzoyl)-6-hexyl-1,2,3,4-tetrahydrocarbazole;

29. 3-diazomethylcarbonyl-9-(4-hexylbenzoyl)-1,2,3,4-tetrahydrocarbazole; and 30. 3-diazomethylcarbonyl-9-(benzoyl)-8-ethyl-1,2,3,4-tetrahydrocarbazole.

Following the procedure described in Example 6 but substituting for 3-diazomethylcarbonyl-9-benzoyl-1,2,3,4-tetrahydrocarbazole an equivalent amount of the diazomethylcarbonyl compounds 25–30 listed above there are obtained respectively:

31. 3-chloromethylcarbonyl-9-benzoyl-6-methyl-1,2,3,4-tetrahydrocarbazole;

32. 3-chloromethylcarbonyl-9-(4-toluoyl)-6-tert-butyl-1,2,3,4-tetrahydrocarbazole;

33. 3-chloromethylcarbonyl-9-(3,4-dimethylbenzoyl)-5,8-dimethyl-1,2,3,4-tetrahydrocarbazole;

34. 3-chloromethylcarbonyl-9-(4-tert-butylbenzoyl)-6-hexyl-1,2,3,4-tetrahydrocarbazole;

35. 3-chloromethylcarbonyl-9-(4-hexylbenzoyl)-1,2,3,4-tetrahydrocarbazole; and 36. 3-chloromethylcarbonyl-9-(benzoyl)-8-ethyl-1,2,3,4-tetrahydrocarbazole.

Following the procedure described in Example 6 but substituting for hydrogen chloride an equivalent amount of hydrogen bromide there is obtained:

37. 3-bromomethylcarbonyl-9-(benzoyl)-1,2,3,4-tetrahydrocarbazole.

Following the procedure described in Example 2 but substituting for ammonium hydroxide an equivalent amount of the following amines: methylamine, dimethylamine, dihexylamine, N-hexyl-N-methylamine and isopropylamine there are obtained respectively:

38. 3-methylaminocarbonyl-9-benzoyl-1,2,3,4-tetrahydrocarbazole;

39. 3-dimethylaminocarbonyl-9-benzoyl-1,2,3,4-tetrahydrocarbazole;

40. 3-dihexylaminocarbonyl-9-benzoyl-1,2,3,4-tetrahydrocarbazole;

41. 3-(N-hexyl-N-methylamino)carbonyl-9-benzoyl-1,2,3,4-tetrahydrocarbazole; and 42. 3-isopropylaminocarbonyl-9-benzoyl-1,2,3,4-tetrahydrocarbazole.

I claim:

1. A 3-Z-9-(R₃-R₄-benzoyl)-R₁-R₂-1,2,3,4-tetrahydrocarbazole having the formula:

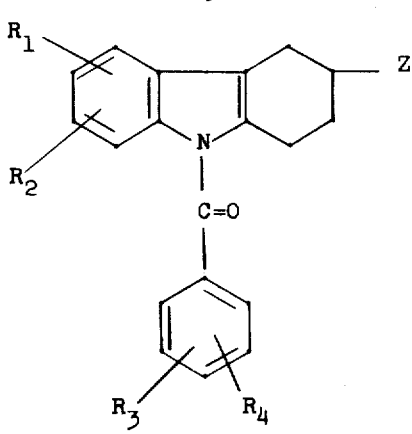

wherein

Z is $COCH_2X$, where $R_1$, $R_2$, $R_3$ and $R_4$ are each hydrogen or lower-alkyl, and X is chloro or bromo.

2. A compound according to claim 1 wherein X is chloro.

3. 3-Chloromethylcarbonyl-9-benzoyl-1,2,3,4-tetrahydrocarbazole according to claim 2.

4. A 3-diazomethylcarbonyl-9-($R'_3$-$R'_4$-benzoyl)-$R'_1$-$R'_2$-1,2,3,4-tetrahydrocarbazole having the formula:

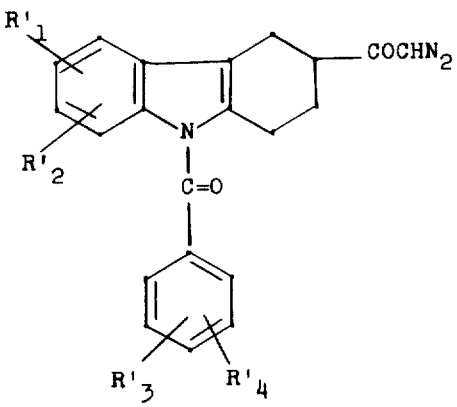

wherein $R'_1$, $R'_2$, $R'_3$ and $R'_4$ are each hydrogen or loweralkyl.

5. 3-Diazomethylcarbonyl-9-benzoyl-1,2,3,4-tetrahydrocarbazole according to claim 4.

* * * * *